United States Patent [19]

Klein et al.

[11] 4,147,782

[45] Apr. 3, 1979

[54] PHARMACEUTICAL DETERGENT COMPOSITION

[75] Inventors: Robert W. Klein, Blue Bell; Mary E. Foxx, Lansdale, both of Pa.

[73] Assignee: William H. Rorer, Inc., Fort Washington, Pa.

[21] Appl. No.: 699,819

[22] Filed: Jun. 24, 1976

[51] Int. Cl.$^2$ .................... A61K 31/60; C11D 7/60
[52] U.S. Cl. .................. 424/230; 252/DIG. 5; 252/14; 252/89 R; 252/173; 252/542; 252/546; 424/317
[58] Field of Search ............ 424/230, 317; 252/89, 252/DIG. 5

[56] References Cited

U.S. PATENT DOCUMENTS

| | | | |
|---|---|---|---|
| 3,109,777 | 11/1963 | Zviak | 424/DIG. 4 |
| 3,968,218 | 7/1976 | Bouillon et al. | 424/DIG. 4 |

OTHER PUBLICATIONS

Soap & Chemical Specialties, 6/1963, p. 171.
Domerine Label 10/1960.
American Medical Assoc. Archives of Dermatology, 6/1958, p. 39.

*Primary Examiner*—Dale R. Ore
*Attorney, Agent, or Firm*—James A. Nicholson; Raymond Underwood

[57] ABSTRACT

Novel pharmaceutical preparation useful for cleaning the skin of persons affected with acne, chronic oily skin and other skin ailments are disclosed.

4 Claims, No Drawings

PHARMACEUTICAL DETERGENT COMPOSITION

This invention relates to detergent compositions and particularly to pharmaceutical preparations for cleansing the skin of persons afflicted with acne, chronic oily skin, and other skin ailments associated with overactive sebaceous glands and an excessively oily skin.

The excessive secretion of sebum presents an unsightly oily appearance on the face, especially about the nose and forehead. Removal of the sebum produces a better cosmetic appearance and is an important contributing factor toward the elimination of skin eruptions, such as acne and certain kinds of dermatitis.

The routine use of soap to remove this oily secretion is not recommended as soaps do not fully cleanse the skin unless the area is bathed at very frequent intervals and considerable frictional, and therefore irritating pressure is applied. In fact, in some instances, it is believed that soap is acnegenic.

Synthetic detergents have been used to cleanse the skin of persons suffering from an exceptionally oily skin and its related disorders, but they cannot be routinely and continuously used as they may cause excessive dryness of the skin or irritation. Most of the pharmaceutical skin detergents cannot be used for extended periods on the face, as the skin is already inflammed to some degree and the harshness of the detergent frequently worsens the condition or precludes the application of primary topical medication.

The detergent compositions of the present invention simultaneously eliminate and overcome the drawbacks of both soap and synthetic detergents. The preparations possess superior skin cleaning properties while retarding the irritating and excessive drying action of soap or conventional skin detergents. One reason for this superiority of the present compositions is that prior detergent mixtures have included oils and so-called, "super fatting" agents as additives in an attempt to replace the natural oils excessively stripped from the skin by the detergents. Such oily ingredients are not only foreign to the natural skin lipids, but they are contraindicated in the treatment of acne and seborrheic conditions of the skin. The compositions of the invention eliminate the need for the inclusion of such oily, lipid substances.

The essential ingredients of the basic detergent system of the invention are: (1) water soluble salts of N-acyl esters of sarcosine, such as formed with sodium, potassium, ammonium, and triethanolamine. Lauroyl is the preferred acyl group.; (2) povidone, which is the generic name for polyvinylpyrrolidones; (3) a protein and/or a protein hydrolysate and (4) water to produce a solution of the ingredients. Other ingredients or agents may be added as will be explained, but the ones just named are essential and a mixture of them will produce a basic effective skin cleanser.

The sarcosine compound is the primary active detergent which effectively removes the oil on the skin without excessively drying the skin. It should constitute from 8 to 31% by weight preferably 15 to 20% of the basic mixture.

The povidone is a polyvinylpyrrolidone having a molecular weight with the range of 15,000 to 90,000. A preferred one is povidone of average molecular weight of 30,000, sold by GAF Inc. Its function in the composition is to aid in cleansing, to form a protective film in the skin and also act as a co-solubilizer for the total composition. As an essential ingredient of the basic composition, it should amount to from 0.1 to 5.0% by weight, preferably 1 to 3%.

The protein or protein-like ingredient is preferably a water-soluble protein hydrolysate and its purpose in the composition is to serve as a natural replacement for the oil removed from the skin, without presenting an oily appearance. Suitable materials are soluble collagen, keratin, protein hydrolysates and peptides such as sodium salt of polypeptides and amino acids, including glycine. As an essential ingredient of the basic composition, it should amount to from 0.1 to 6.0% by weight, preferably 1 to 4% of the final composition. The remainder of the basic composition is deionized or distilled water. A surprising advantage of this composition is that the combination of the three essential ingredients simultaneously facilitates and improves the cleansing and oil removing capacity, while preventing excess dryness of the skin, even when utilized routinely, three times daily.

Although it is not essential to a satisfactory composition, it is preferable that the pH of the composition be adjusted within the range of 4.6 to 8.3 by the addition of a conventional acidifying or alkalizing agent. Its selection will largely depend on the protein or protein-like material which is used. It is preferred that the range be within the limits of pH 4.9 to 6.1 and for this purpose it is advisable to use buffers such as citric and lactic acid and their salts. This may call for the addition of an amount of the selected acid and/or salt, so that it constitutes from 0.5 to 3.0% of the final weight of the composition, so that it replaces part of the water to be used.

To make the basic compositions, the three essential ingredients are weighed out and thoroughly mixed with the measured amount of water. Some of this solution is dispensed in the hands or on a washcloth and the face is washed in a normal manner and rinsed off with a small amount of water. Some of the povidone and protein or protein-like material will remain on the face. As has been stated above, it is advisable to adjust the composition to a pH, as mentioned above, which is compatible with the face by addition of the agents mentioned above.

A further surprising advantage of the basic composition described above is that, to it may be added a keratolytic organic agent and obtain a stabilized composition. Such keratolytic agents are applied to the skin to assist in the keratolysis or softening and peeling of the thickened or horny layer of the epidermis. A frequently used keratolytic agent is salicylic acid, but its use has been limited because in the presence of a phenolic detergent and also a solubilizing agent such as Polysorbate, for the insoluble salicylic acid, a complexing occurs between these agents and the salicylic acid. This complex serves to deactivate or inactivate both the detergent and the salicylic acid so that both the antiseborrheic and the keratolytic activities are minimized or lost.

The formation of an undesirable complex is not produced in the present composition, and solubilizing agents such as polyethylene glycol and its derivatives, and Polysorbate 80 are not needed to make a clean water solution of the keratolytic agent. As is stated above, the basic composition of a sarcosinate, povidone and a protein or protein-like substance, is compatable with salicylic acid so that the addition of the latter results in a stable composition. The salicylic acid may constitute from 0.1 to 5.0% by weight, preferably 2 to 3% of the total aqueous composition.

Other agents may be added to the composition, but they are not essential and representative ones are the following:

1. Foam boosters and stabilizers such as fatty acid amides and fatty alkyl amines and their derivatives. Representative substances are lauric diethanolamide, myristic diethanolamide and stearyl alkyl amine. The foam producer should amount to 1 to 3% by weight of the total composition.

2. Preservatives such as antibacterial/antifungal agents; useful ones are methyl parabens and propyl parabens. It should constitute from 0.1 to 0.3% of the total composition.

3. Chelating agents such as ethylenediaminetetraacetic acid (edetic acid) and citric acid. It should amount to from 0.05 to 0.2% of the total composition.

4. Fragrance, such as perfume, of choice.

5. Nonionic and/or anionic compatible detergents.

Any one or more of these elective, non-essential agents may be added with the water along with the essential ingredients mentioned above which make up the basic composition. Additional electives may be added as is obvious to those trained in the art of cosmetic and dermatologic formulating, etc.

Representative examples are the following.

EXAMPLE 1

| A basic composition is the following: | % by weight |
|---|---|
| TEA N-Lauroyl sarcosinate, 40% | 20 |
| Povidone K-30 | 2 |
| Protein hydrolysate | 2 |
| Water, distilled or deionized | 76 |

EXAMPLE 2

The amount of sarcosinate in Example 1 is as low as 8% up to as high as 31%, the amount of water being correspondingly increased or decreased.

EXAMPLE 3

In Example 1, the amount of povidone is within the range of 0.1 to 5.0% by weight.

EXAMPLE 4

In Example 1, the amount of protein hydrolysate is within the range of 0.1 to 6.0% by weight.

EXAMPLE 5

|  | % by weight |
|---|---|
| Sodium N-Lauroyl Sarcosinate | 20 |
| Povidone K-30 | 2 |
| Protein (Water soluble or dispersable | 2 |
| Water, distilled or deionized | 76 |

EXAMPLE 6

| Tea N-Lauroyl sarcosinate | 15 |
|---|---|
| Providone K-30 | 1 |
| Protein hydrolysate | 1 |
| Lauric diethanolamide | 2 |
| Edetic acid | 0.1 |
| Methyl paraben | 0.15 |
| Water | 80.75 |

EXAMPLE 7

| TEA N-Lauroyl sarcosinate | 15 |
|---|---|
| Providone K-30 | 1 |
| Protein hydrolysate | 1 |
| Lauric diethanolamide | 2 |
| Edetic acid | 0.1 |
| Methyl paraben | 0.15 |
| Water | 75.75 |
| Salicylic acid | 3 |

EXAMPLE 8

| TEA N-Lauroyl sarcosinate | 15 |
|---|---|
| Providone K-30 | 1 |
| Protein hydrolysate | 1 |
| Lauric diethanolamide | 2 |
| Edetic acid | 0.1 |
| Methyl paraben | 0.15 |
| Lactic acid | 3 |
| Water | 75.75 |

EXAMPLE 9

| TEA N-Lauroyl sarcosinate | 15 |
|---|---|
| Povidone K-30 | 1 |
| Protein hydrolysate | 1 |
| Lauric diethanolamide | 2 |
| Edetic acid | 0.1 |
| Methyl paraben | 0.15 |
| Citric acid | 0.5 |
| Water | 80.25 |

Tests for safety and irritation of the antiseborrheic detergent cleanser established that the combination effectively acts as a potent antiseborrheic agent, reducing the oil level of the skin without causing the expected red flareup and dry, peeling and flaking upon prolonged usage. The unique vehicle apparently protects the skin from overreacting with the dissolved antiseborrheics. Theoretically, the skin substantivity of the sarcosine-PVP-protein system is greater than the affinity of the skin for the dissolved keratolytic. This forms a protective "film" preventing residual antiseborrheic material from remaining directly on the skin in microquantities after rinsing. Conventional detergent systems allow keratolytics to plate out substantively on the skin. Trace residues left behind, after rinsing the skin, continue to dry, irritate and often peel the skin surface when used routinely.

We claim:

1. An aqueous pharmaceutical detergent composition for cleansing oily skin which comprises the following ingredients, by weight:

| N-Acyl ester sarcosinate salt in which the salt moiety is selected from sodium, potassium, ammonium and triethanolamine and in which the acyl ester moiety is selected from lauroyl, myristoyl and stearoyl | 8.0 to 31.0 |
|---|---|
| Polyvinyl pyrrolidone having an average molecular weight of 4000 to 90,000 | 0.1 to 5.0 |
| Water soluble protein hydrolysates | 0.1 to 6.0 |

| | |
|---|---|
| Water | Q.S. |

2. The composition of claim 1 in which the pH is adjusted within 4.6 and 8.3.

3. The composition of claim 1 which also includes a keratolytic agent selected from the group consisting of salicylic acid, and lactic acid in an amount to constitute from 0.1 to 6.0% by weight of the composition.

4. The composition of claim 1 which additionally includes an agent selected from the group consisting of a fatty acid amide, a fatty alkylamine, propyl dimethyl amine oxide, citric acid, a nonionic detergent and an anionic detergent.

* * * * *